United States Patent [19]
Spahn et al.

[11] Patent Number: 5,324,414
[45] Date of Patent: Jun. 28, 1994

[54] ION SELECTIVE ELECTRODE

[75] Inventors: Robert G. Spahn; Louis J. Gerenser, both of Webster, N.Y.

[73] Assignee: Eastman Kodak Company, Rochester, N.Y.

[21] Appl. No.: 889,827

[22] Filed: Jun. 1, 1992

[51] Int. Cl.$^5$ .......................... G01N 27/333
[52] U.S. Cl. .................... 204/416; 204/177; 204/418; 204/435
[58] Field of Search ............ 204/416, 418, 419, 435

[56] References Cited

U.S. PATENT DOCUMENTS

| | | | |
|---|---|---|---|
| 3,686,018 | 8/1972 | Lindblom et al. | 117/47 |
| 4,454,007 | 6/1984 | Pace | 204/418 |
| 4,816,341 | 3/1989 | Nakayama et al. | 428/458 |
| 4,886,681 | 12/1989 | Clabes et al. | 427/38 |

FOREIGN PATENT DOCUMENTS 57-187327 11/1982 Japan.

OTHER PUBLICATIONS

Gerenser, "Photo Emission Investigation of Silver/Poly(ethylene terephthalate) Interfacial Chemistry: The Effect of Oxygen-Plasma Treatment", J. Vac. Sci. Tech., vol. 8, No. 5, (Sep.-Oct. 1990).

Burger & Gerenser, "Understanding the Formation and Properties of Metal/Polymer Interfaces via Spectroscopic Studies of Chemical Bonding", Soc. of Vac. Coaters, 34th Ann. Tech. Conf. Proceedings, 1991.

Gerenser, Metallization of Polymers, Am. Chem. Society Symposium Series, No. 440, Chap. 32, "X-ray Photoelectron Spectroscopy of Modified Polymer Surfaces and Metal-Polymer Interfaces", pp. 433–452, 1990.

"An X-Ray Photoeission Spectroscopy Study of Chemical Interactions at Silver/Plasma Modified Polyethylene Interfaces: Correlations with Adhesion", Gerenser, S. Vac. Sci. Technol., vol. 6, No. 5, (Sep./Oct. 1988).

Primary Examiner—T. Tung
Attorney, Agent, or Firm—John R. Everett

[57] ABSTRACT

A method is disclosed for producing Ag/Ni composite ion selective electrode on polymer substrates. By utilizing a nitrogen glow discharge pretreatment of the polymer substrate, silver may be deposited directly thereon. Further, because of the glow discharge pretreatment, aging of the silver layer prior to nickel deposition and bleaching operation is not necessary.

3 Claims, 1 Drawing Sheet

ION SELECTIVE ELECTRODE

FIELD OF THE INVENTION

The present invention relates to a method of producing an ion selective electrode, in particular ion selective electrodes having Ag/Ni deposited films.

BACKGROUND OF THE INVENTION

Ion selective electrodes (ISE) are used in the medical field, for example as blood analyzer assays. The particular ISE which the present invention is primarily concerned with is a multi-layer ISE having vacuum deposited Ag/Ni coatings deposited on a plastic substrate. U.S. Pat. No. 4,214,968, the disclosure of which is hereby incorporated by reference, discloses such ISE's and methods for their manufacture. A particular preferred substrate for the present invention is polyethylene terephthalate (PET).

Prior to the process of the present invention, the method of manufacturing Ag/Ni electrodes consisted of first providing a PET substrate with an adhesion promoting sub-coating thereon, such as poly(acrylonitrite-co-vinylidene chloride-co-acrylic acid), to improve the adhesion between the PET substrate and the deposited metal layers. A silver layer was then vacuum deposited over the sub-coating. Prior to the subsequent step of depositing nickel, the silver layer required aging of approximately 10 weeks. After the aging process, nickel was selectively deposited in a striped formation over the silver layer. The exposed silver areas were then exposed to a bleaching agent which converted a portion of the silver layer to AgCl. If the silver was not aged sufficiently prior to the Ni deposition step, then during the bleaching operation cracking would frequently occur in the silver layer between the nickel stripes, rendering the electrode useless. The mechanism which caused the cracking is unknown. Since the cracking occurred regardless of whether the adhesion promoting sublayer was employed and in fact occurred even on electrodes that exhibited relatively good PET-/Ag adhesion, the cracking did not seem to be adhesion related. Consequently, prior to the nickel deposition, to achieve the requisite aging, the silver deposited on the PET substrate required storage for some 10 to 12 weeks, greatly increasing manufacturing cost. Further, prior to the present invention, an adhesion promoting sublayer, mentioned above, was needed to prevent both cracking and delamination of the electrode during manufacture.

Glow discharge pretreatment and similar techniques are known techniques for improving the adhesion between polymer substrates and metal coatings deposited by physical deposition processes. However, there is no teaching that such a pretreatment in a nitrogen atmosphere will prevent cracking of the silver layer in a Ag/Ni electrode, even though the nickel layer is applied without substantial prior aging of the silver layer.

High energy ion beams have been used to enhance the adhesion between deposited metal layers and organic substrates. In ion beam enhanced adhesion, a high energy beam of ions is incident upon the organic substrate prior to deposition of a metal layer. For example, copper can be deposited on polymer substrates by electron beam deposition, after high energy ion irradiation of the substrates. In this procedure, both reactive and inactive ions can be used, and the ion beam energy ranges upward from about 200 keV.

Such systems are costly and require complicated apparatus to produce the high energy, focused ion beam. The nature of the ion beam makes it impossible to be able to process large substrate areas simultaneously, and therefore this technique is not readily suitable for high throughput in commercial systems. Further, high energy ion beams can cause damage to the organic substrate and require large amounts of power. It is also extremely difficult to make large, high energy ion beams with the proper flux and power over a large area.

Glow discharge or plasma discharge has also been used to affect the polymer surface prior to metal deposition. In glow discharge techniques, a brush or glow discharge is created by introducing residual gasses into a vacuum chamber and applying a high voltage in order to create ions which activate the polymer substrate surface. Examples of the gasses which can be introduced into the vacuum chamber include air, oxygen, nitrogen, helium, neon, argon, krypton, xenon, and radon. After the glow discharge activation, the metal film is deposited by techniques such as electroless plating, evaporation, and sputtering.

A method for producing Ag/Ni ion selective electrodes is needed which does not require long aging periods for the Ag layer prior to the Ni deposition and bleaching operation. Ideally, the process should be one in which the Ag and Ni layers can be deposited within a short period of time, and ideally where they can be deposited during one manufacturing operation, after which the PET/Ag/Ni apparatus can be immediately bleached.

SUMMARY OF THE INVENTION

The present invention comprises subjecting at least one surface of a polymeric substrate to a glow discharge plasma in an atmosphere containing nitrogen gas and thereafter depositing a layer of silver on said treated surface.

The method of the present invention may be used to produce electrochemical analysis elements such as ion selective electrodes. The method for producing ion selective electrodes comprises subjecting at least one surface of a polymeric substrate to a glow discharge plasma in an atmosphere containing nitrogen gas, depositing a layer of silver on the treated polymeric surface, depositing a conductive metal on selected areas of the silver layer, thereby leaving uncoated areas of silver, and exposing the uncoated areas of the silver layer to a bleach bath to convert a portion of the silver layer to a silver halide. A preferred conductive metal is nickel. The conductive metal deposition and bleaching steps may be performed immediately after silver deposition. Optimally, a portion of the uncoated areas of the silver may be coated with various ion transport facilitating gel compositions, or a protective material, such as cellulose acetate.

The ion selection electrode of the present invention comprises a polymeric substrate having a major surface whose composition contains nitrogen and a layer of a silver containing material deposited directly on the polymeric substrate, selected areas of the silver layer comprising a silver halide, the remainder of the silver layer comprising silver metal areas. Preferably, the ion selective electrode also comprises a layer of a conductive metal selectively deposited over the silver metal areas. The preferred conductive metal for this purpose is nickel. The ion selective electrode may also comprise a layer of an ion transport facilitating material or a protective material selectively deposited over said silver halide.

DETAILED DESCRIPTION

In accordance with the method of the present invention, it has been discovered that, by pretreating a PET substrate by glow discharge in a nitrogen containing atmosphere, silver and nickel coatings may be deposited in immediate successive deposition operations, without the need for substantial aging of the silver layer prior to deposition of the nickel layer. The composite structure may then be immediately bleached to convert a portion of the silver to a silver halide. By using a low energy glow discharge in a nitrogen containing atmosphere to treat the organic substrate the surface chemistry of the substrate is altered to include nitrogen in its structure. In distinction from many ion beam energy techniques of the prior art, the present invention requires the presence of nitrogen in the glow discharge atmosphere.

The preferred ion selective electrode (ISE) of the present invention consists of a polymeric substrate, to which is directly deposited a layer of Ag. A layer of nickel is selectively deposited over the silver layer. The composite structure is then bleached to convert a portion of the silver layer to a silver halide, such as AgCl. Thus, the ISE of the present invention utilizes no adhesion promoting sublayer. Alternatively, the AgCl may be covered with gels and a protective or ion selective membrane.

The substrates are organic materials including plastics, polyimide, polyesters, Mylar (a trademark of E. I. duPont DeNemours), epoxies, etc. Typically, the substrates are organic polymers. A preferred substrate is poly(ethylene terephthalate)(PET).

Substrate treatment and metal deposition can occur over a range of temperatures, including room temperature and elevated temperatures. Commercially available apparatus can be used to provide the glow discharge pretreatment as well as the metal deposition steps, which are preferably dry processing steps, in particular e-beam evaporation. In contrast with prior manufacturing operations, no adhesion promoting layer is applied prior to silver deposition, and yet increased performance of the resultant multi-layer film is exhibited even over those films that were deposited using adhesion promoting sublayers. In particular, there is no evidence of cracking of the silver layer during the bleaching operation, even though the operation may be conducted within days, and preferably immediately after silver deposition. This is particularly significant because prior to the method of the present invention, the cracking problem was only avoidable by aging the silver layer for approximately 10 weeks.

Figure 1:
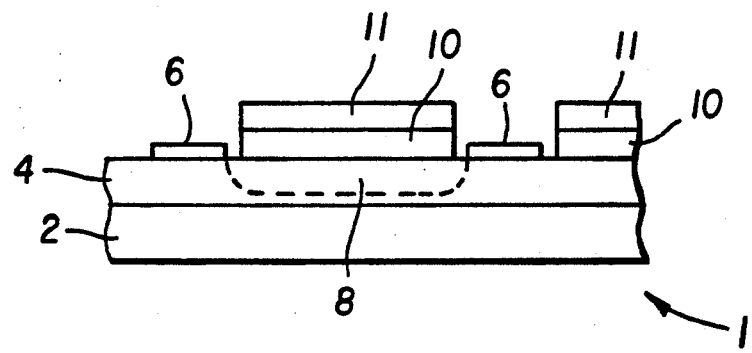
FIG. 1 illustrates a Ag/Ni ion selective electrode produced in accordance with the present invention.

A silver/nickel ion selective electrode produced in accordance with the present invention is illustrated in FIG. 1. The electrode 1 typically includes a PET substrate 2, which, after being treated by a nitrogen glow discharge, has a coating of silver 4 deposited thereon. Prior art devices usually utilize an adhesion promoting sub-layer between the silver and the PET substrate. However, because of the nitrogen glow discharge pretreatment there is no need for an adhesion promoting layer in the present invention. A series of nickel stripes 6 is selectively deposited over the silver layer 4, after which the entire operation is exposed to a bleaching solution which converts a portion 8 of the silver layer 4 to silver chloride. The apparatus of this point is operable as a chloride ion sensitive electrode. Alternatively, various ion selective gels or membranes 10 may be selectively applied over the silver chloride portion 8 to make the ISE sensitive to various other ions. For an explanation of examples of such gels and membranes, see U.S. Pat. No. 4,214,968.

An apparatus 20 suitable for carrying out the method of the present invention to manufacture ISEs is illustrated in FIG. 1. The apparatus 20 as illustrated is a single in-line vacuum web coating apparatus. Consequently, the apparatus 20 has a glow discharge subchamber 22, a silver deposition chamber 24 having a silver source crucible 25, and a nickel deposition chamber 26 having a nickel source crucible 27. Of course, more deposition chambers could be utilized if desired. Alternatively, both chamber 24 and 26 could be used to deposit first Ag, after which crucibles 25 and 27 could be changed to deposit nickel. A vacuum pump 28 is connected to the apparatus 20 to achieve a suitable pressure, preferably below $7 \times 10^{-3}$ Pascals. Glow discharge chamber 20 is similar to many conventional sputtering subchambers, and includes a conventional cathode 30, and is supplied with a nitrogen containing atmosphere via gas inlet 31. Cathode 30 is preferably made of a material having a low sputtering coefficient to prevent sputtering of the cathode material onto the plastic substrate during the glow discharge pretreatment. Examples of materials having a low sputtering coefficient include aluminum and stainless steel.

A substrate material 32, which is stored on input roller 34, is fed first into the glow discharge chamber 22, where it receives a glow discharge treatment in the presence of nitrogen, as discussed above. Subsequent analysis of the substrate by X-ray photoelectron spectroscopy (XPS) indicates that such a plasma treatment results in nitrogen being chemically incorporated into the surface structure of the substrate at specific sites. In the case of PET, the nitrogen typically reacts with organic materials in the PET to form nitrogen amines, imines and amides. The substrate is then transported to the coating chambers 24 and 26, where the Ag and Ni layers are applied, after which the substrate is wound onto output roller 43. The silver and nickel deposition chambers 24 and 26 are similar to conventional e-beam evaporation apparatus, and include, for example, a conventional e-beam gun and crucible which holds the metal to be deposited.

A water cooled mask 44 is provided in the nickel deposition chamber 26 to mask areas of the PET substrate 29 when desired, so that, for example, the nickel can be selectively applied in a striped configuration as described above.

The principle of plasma treatment will be briefly described. When an electric filed is applied to a gas kept at a reduced pressure, free electrons which are present in a minor proportion in the gas and have a remarkably greater inter-molecular distance than under atmospheric pressure are accelerated under the electric field to gain a kinetic energy (electron temperature). These accelerated electrons collide against atoms and molecules to fracture their atomic and molecular orbitals to thereby dissociate them into normally unstable chemical species such as electrons, ions, neutral radicals, etc. The dissociated electrons are again accelerated under the electric field to dissociate further atoms and molecules. The chain reaction causes any gases present to be instantaneously converted into a highly ionized state. This is generally called a plasma. Since gaseous molecules have less chance of collision with electrons and absorb little energy, they are kept at a temperature approximate to room temperature. Such a system in which the kinetic energy (electron temperature) of electrons and the thermal motion (gas temperature) of molecules are not correlated is designated as a low temperature plasma.

Glow discharge pretreatment of prior art devices usually involve oxygen, commonly up to 100%, as the active component of the atmosphere during glow discharge. However, atmospheres containing oxygen are not preferred for the method of the present invention. The preferred glow discharge atmosphere of the present invention is one containing nitrogen. The remainder of the atmosphere may consist of an inert gas. A preferred inert gas is argon. Thus, for example, a suitable atmosphere for carrying out the glow discharge pretreatment step in accordance with the present invention is an atmosphere of 98% argon and 2% nitrogen.

Because nitrogen is incorporated into the polymer surface, covalent bonding can occur between the silver coating and the modified polymer structure. It is believed that this phenomena is responsible for the increased adhesion of the silver layer inherent with the ISEs of the present invention. More importantly, however, when prepared using the glow discharge pretreatment described herein, the silver layer exhibits no cracking during the bleaching operation of the manufacturing process.

It should be noted that adhesion of Ag to the PET layer after glow discharge treatment does fall off with time. For example, there is a noticeable decrease in adhesion if a waiting period of 10 hours or more occurs prior to silver coating deposition. Therefore, ideally the manufacturer of the ion selective electrode of the present invention should take place in successive steps, preferably within the same apparatus. However, this is not essential to the practice of the invention, and thus the invention can be carried out in separate apparatus and also with or without a short waiting period prior to nickel deposition.

The beneficial effect of nitrogen glow discharge is dependent upon system parameters, which include, for example, the geometry of the chamber, nitrogen content and pressure in the chamber, and cathode power. Another important variable is treatment energy E, which is equal to the power applied to the cathode (in watts) $\times$ exposure time $\div$ cathode area. For a given glow discharge chamber, below a certain threshold treatment energy, the nitrogen glow discharge will not alleviate the cracking phenomena. On the other hand, above a certain treatment energy, damage will occur to the substrate.

For the particular glow discharge apparatus described herein, which is a parallel plate chamber (cathode is parallel to the substrate surface) having a cathode to substrate distance of about 12.7 cm and a cathode area of about 329 cm$^2$, vacuum base pressure during glow discharge pretreatment is preferably maintained at about the $7 \times 10^{-3}$ Pascals range or lower. More preferably, the base pressure is maintained below $1 \times 10^{-3}$ Pascals. During the glow discharge treatment, pressure in the glow discharge chamber is typically 1 to 67 Pascals, and preferably 6.7 to 14 Pascals. The voltage applied to create the glow discharge plasma when such pressures are used is in the range of 700 to 1200 volts. The voltage applied is relatively low in order to avoid deposition of the cathode material, which is purposefully chosen to have a low sputtering coefficient for the same reason. These parameters result in a treatment energy between about 1.1 and 4 joules/cm$^2$.

After glow discharge pretreatment of the PET substrate, a 600 to 800 nanometer thick film of silver metal is deposited on the PET substrate in deposition chamber 24. A preferred method for deposition of the silver layer is e-beam evaporation. Electron beam vacuum evaporation is a standard deposition technique wherein vapors are produced from material located in a source (usually a crucible filled with the material to be deposited) which is heated by direct impingement by a stream of electrons from an electron beam gun. For example, see Maissel & Glang, Handbook of Thin Film Technology, Part 1, Section 21, pp 53–54. The silver metal then vaporizes, and rises upwardly, where it deposits on the PET substrate. The process is usually carried out in vacuum (typically $10^{-2}$ to $10^{-3}$ Pascals) so the evaporated atoms undergo an essentially collision-less line of sight transport prior to condensation on the substrate.

In the preferred embodiment of the invention, after deposition of the silver coating, stripes of nickel are deposited in deposition chamber 26, by e-beam evaporation, at a thickness of 12 to 20 nanometers. A water-cooled mask 44 prevents deposition in selected areas, thereby resulting in a striped nickel coating.

After deposition of the nickel stripes, the exposed portions of the silver layer are subjected to a bleaching agent, such as, for example, a solution of potassium chloride and potassium chromate (not shown). Bleaching as used herein and in the claims is a technique used to convert a portion of the silver layer to a silver halide, such as AgCl. The bleaching step is used to convert approximately 25–40 percent of the thickness of the silver layer in the exposed areas to silver chloride, as indicated by 8 in FIG. 2. The percentage of the thickness of AgCl converted depends upon the desired end use of the ISE. For example, for chloride ISEs, about 36 percent of the thickness is converted, and for sodium ISEs, about 26 percent of the thickness of the Ag layer is converted to AgCl. The areas of the silver layer under the silver coated stripes remain essentially unchanged.

When prepared in accordance with the present invention, the composite Ag/Ni coatings of the present invention exhibit no vertical cracking of the AgCl layer during bleaching, even though no aging of the Ag is required prior to Ni stripe deposition, and even though no adhesion promoting layer is applied to the PET substrate. Consequently, the composite ISE of the present invention can be produced using less materials and in less manufacturing operations (no aging of Ag step). Perhaps more importantly, the present invention alleviates the need for an inventory system, storage facility, etc., needed to facilitate aging of the silver layer.

The PET/Ag/AgCl/Ni composite thus formed is operable as a chloride ion selective electrode. A protective overcoat may be selectively coated over the composite device. For example, cellulose acetate may be applied over the AgCl portion in a chloride ion sensitive electrode.

To produce other ion sensitive electrodes (such as potassium or sodium ISEs) using the PET/Ag/AgCl/Ni composite of the present invention, a further step may be conducted in which areas of the silver chloride are selectively overcoated with an electrolyte containing gel and an ion selective membrane, such as, for example, is indicated by 10 and 11, respectively, in FIG. 1. Conventional ion selective membranes are materials which incorporate hydrophobic polymers in combination with an ionophoric (facilitates ion transport) material. Examples of electrolyte containing gels are NaCl containing gels (for Na ISE's) and KCl containing gels (for K ISE's). Examples of such ion selective membranes are those that contain valinomycin (for K ISE's) and methyl monensin (for Na ISE's). For further explanation see U.S. Pat. No. 4,214,968, which was incorporated by reference hereinabove. Electrodes produced in connection with the present invention perform as well as electrodes prepared in accordance with prior art methods, even though no adhesion layer was included on the PET substrate, and there was no aging of the silver layer prior to nickel deposition.

The invention may be more easily comprehended by reference to specific examples. It must be understood, however, that these examples are provided only for purposes of illustration, and that the invention may be practiced otherwise than as specifically illustrated without departing from its spirit and scope.

EXAMPLE 1

Figure 2:
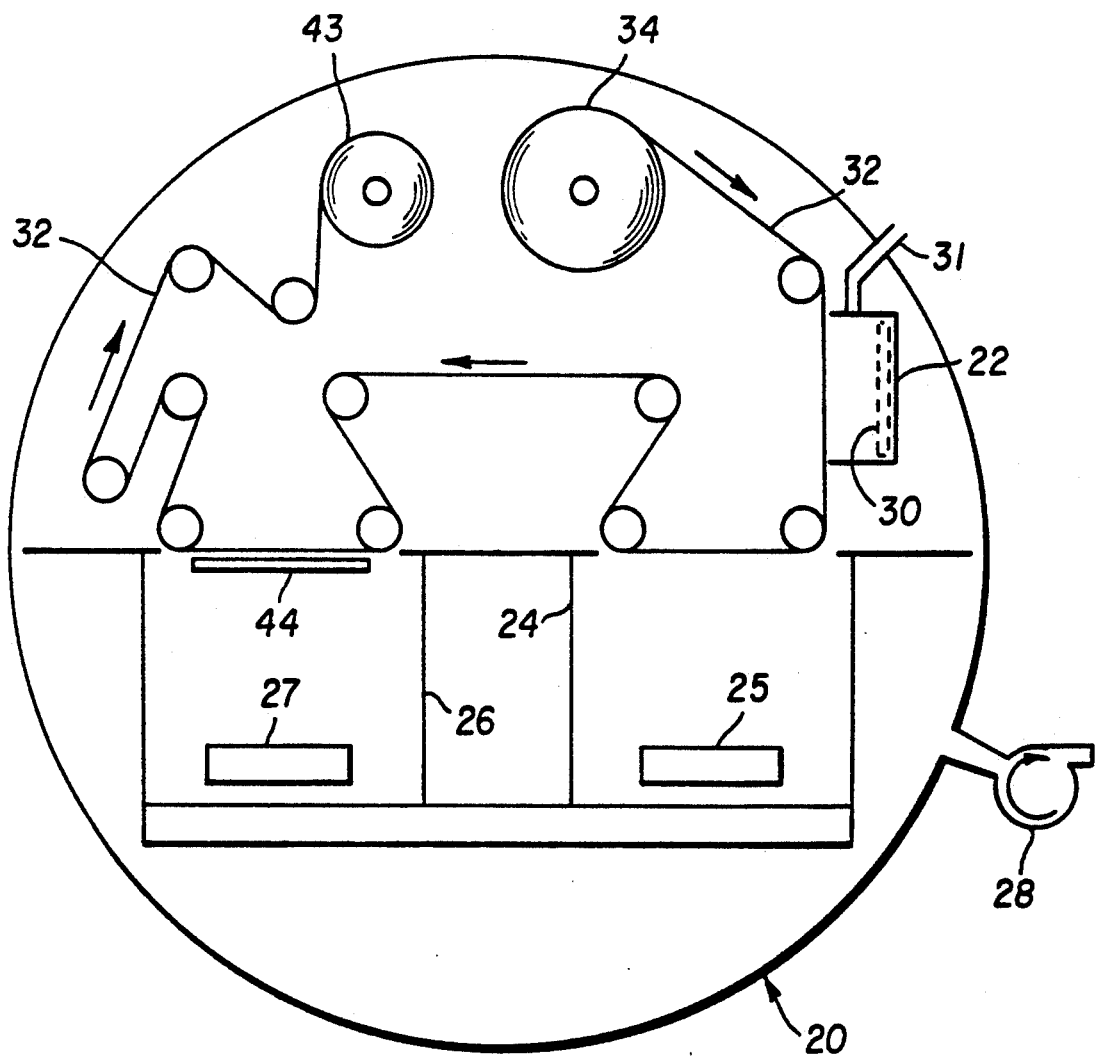
FIG. 2 schematically illustrates an apparatus for carrying out the method of the present invention.

A vacuum web coating apparatus 20 similar to that illustrated in FIG. 2 was evacuated to a base pressure of about $5.3 \times 10^{-4}$ Pascals. A roll of approximately 175 nm thick poly(ethylene terephthalate) (PET) film substrate (having no adhesion promoting sublayer thereon) was unrolled and transported through the coater, traveling first through a glow discharge chamber 22 where it was subjected to a glow discharge pretreatment. The atmosphere during the glow discharge pretreatment step was 100 percent nitrogen. The nitrogen gas was bled into chamber 22 at a pressure of 6.65 Pascals. The glow discharge cathode was then activated at a power chosen to give a treatment energy of 1.5 joules/cm$^2$ (as calculated from $E=W*t/A$, where $W=90$ watts total cathode power, $A=329$ cm$^2$ cathode area, and $t=5.4$ seconds exposure time of a given area of the support to the glow discharge).

After the glow discharge treatment, the PET support was transported to deposition chambers 24 and 26, each of which were set up to deposit silver (thus no mark 44 was employed). A layer of metallic silver approximately 700 nm thick or 7.35 g/m$^2$ was deposited by electron-beam gun vacuum evaporation of a silver metal contained in crucible 25.

Within 8 hours the silver film above coated was overcoated with a series of parallel nickel stripes, approximately 8.4 mm wide and 12 nm thick, separated by 23.4 mm wide uncoated spaces. The nickel layer 8 was also applied by electron-beam gun evaporation from a nickel source in a vacuum web coater using standard technique as described above.

The Ni coated film was then treated with an aqueous solution of 8.45 g/l potassium chlorochromate as described in U.S. Pat. No. 4,214,968, Example 2. This process converted approximately 36 percent of the thickness of the silver layer in the non-Ni-striped areas to silver chloride as indicated by 8 in FIG. 1. The areas of the silver layer under the nickel coated stripes remained essentially unchanged.

Surface examination of the electrode samples with a low power 50× reflecting microscope revealed absolutely no cracking in the silver-silver chloride layer.

The resulting composite ISE gave excellent response, i.e., essentially equal to controls prepared using prior art processes of manufacture.

A 'tape test' was used to evaluate adhesion of the layers. A piece of cellulose adhesive tape was applied to the top electrode surface using finger pressure, then quickly pulled off. Tests with repeated samples of this electrode showed no separation of layers and the electrode structure invariably remained intact.

Comparative Example 1

This example, which illustrates the prior method of manufacture, is virtually the same as Example 1, only the PET substrate had an adhesion promoting sublayer applied thereon. A 175 nm thick PET film having an adhesion promoting sublayer thereon of poly(acrylonitrile-co-vinylidene chloride-co-acrylic acid) was used as the substrate. After being coated with a 700 nm thick silver layer, metallic nickel stripes approximately 12 nm thick were deposited within a period of 8 hours. The composite material was then subjected to the same bleaching process described in Example 1. Examination of the surface of the material with a low power (50×) reflecting microscope after bleaching revealed extensive cracking of the silver-silver chloride layer in between the nickel metal stripes. The cracks were oriented essentially perpendicular to the nickel stripes and the substrate and continued through to the base.

Although nickel stripes are preferred in the electrodes of the invention, in the ISEs described above other conductive metals, such as, for example, Ti, alloys of conductive metals, etc., can be substituted for the nickel stripes. Further, an operable ISE can be configured without any conductive metal stripes. Thus, for example, the present invention can be utilized to manufacture an ISE comprising a AgCl layer over a Ag metal layer on a plastic substrate, with no conductive metal stripes thereon, such as is disclosed in U.S. Pat. No. 4,214,968. The invention has been described in detail with reference to preferred embodiments thereof, but it will be understood that variations and modifications can be effected within the spirit and scope of the invention.

We claim:

1. An ion selective electrode comprising:
   a poly(ethylene terephthalate) substrate having a major surface containing nitrogen;
   a layer of a silver containing material deposited directly on said major surface of said substrate, selected areas of said silver layer comprising a silver halide, the remainder of said silver layer comprising silver metal areas and a layer of nickel metal selectively deposited over said silver metal areas.

2. The element of claim 1, further comprising a layer of an electrolyte containing material selectively deposited over said silver halide; and
   a layer of an ion selective material deposited over said electrolyte containing material.

3. The element of claim 1, further comprising a protective material deposited over said silver halide areas.

* * * * *